(12) United States Patent
Carroll

(10) Patent No.: US 9,259,420 B2
(45) Date of Patent: Feb. 16, 2016

(54) TETRANDRINE PHARMACEUTICAL FORMULATIONS

(71) Applicant: Ron D. Carroll, Fayetteville, NY (US)

(72) Inventor: Ron D. Carroll, Fayetteville, NY (US)

(73) Assignee: CBA Pharma, Inc., Lexington, KY (US)

( * ) Notice: Subject to any disclaimer, the term of this patent is extended or adjusted under 35 U.S.C. 154(b) by 0 days.

(21) Appl. No.: 14/025,080

(22) Filed: Sep. 12, 2013

(65) Prior Publication Data

US 2014/0135354 A1 May 15, 2014

Related U.S. Application Data

(60) Provisional application No. 61/700,701, filed on Sep. 13, 2012.

(51) Int. Cl.
*A61K 31/47* (2006.01)
*A61K 31/4745* (2006.01)
*A61K 31/4741* (2006.01)

(52) U.S. Cl.
CPC ......... *A61K 31/4745* (2013.01); *A61K 31/4741* (2013.01)

(58) Field of Classification Search
CPC .................. A61K 31/4725; A61K 31/4741
See application file for complete search history.

(56) References Cited

U.S. PATENT DOCUMENTS

| 5,025,020 A | 6/1991 | Van Dyke |
| 6,124,315 A | 9/2000 | Van Dyke |
| 6,528,519 B1 | 3/2003 | Van Dyke |
| 6,911,454 B1 | 6/2005 | Van Dyke |
| 6,962,927 B1 | 11/2005 | Van Dyke |
| 2008/0268036 A1 | 10/2008 | Guy et al. |

FOREIGN PATENT DOCUMENTS

| CN | 1729981 A | * | 2/2006 |
| KR | 2007113532 A | * | 11/2007 |

OTHER PUBLICATIONS

English-translation of CN 1729881 A and its abstract (Feb. 2006).*
English-translation of KR 2007113532A (Nov. 2007).*
Xiaoyan et al., "Preparation of chitosan gelatin scaffold containing tetrandrine-loaded nano-aggregates and its controlled release behavior," International Journal of Pharmaceutics 350 (2008) 257-264.

* cited by examiner

*Primary Examiner* — Kevin E Weddington
(74) *Attorney, Agent, or Firm* — Mitchell Intellectual Property Law, PLLC

(57) ABSTRACT

Drug formulations, methods and their use in treatment of diseases using the free base formulations of tetrandrine family members, especially d-tetrandrine, combined with a pharmaceutical diluent or carrier.

5 Claims, 6 Drawing Sheets

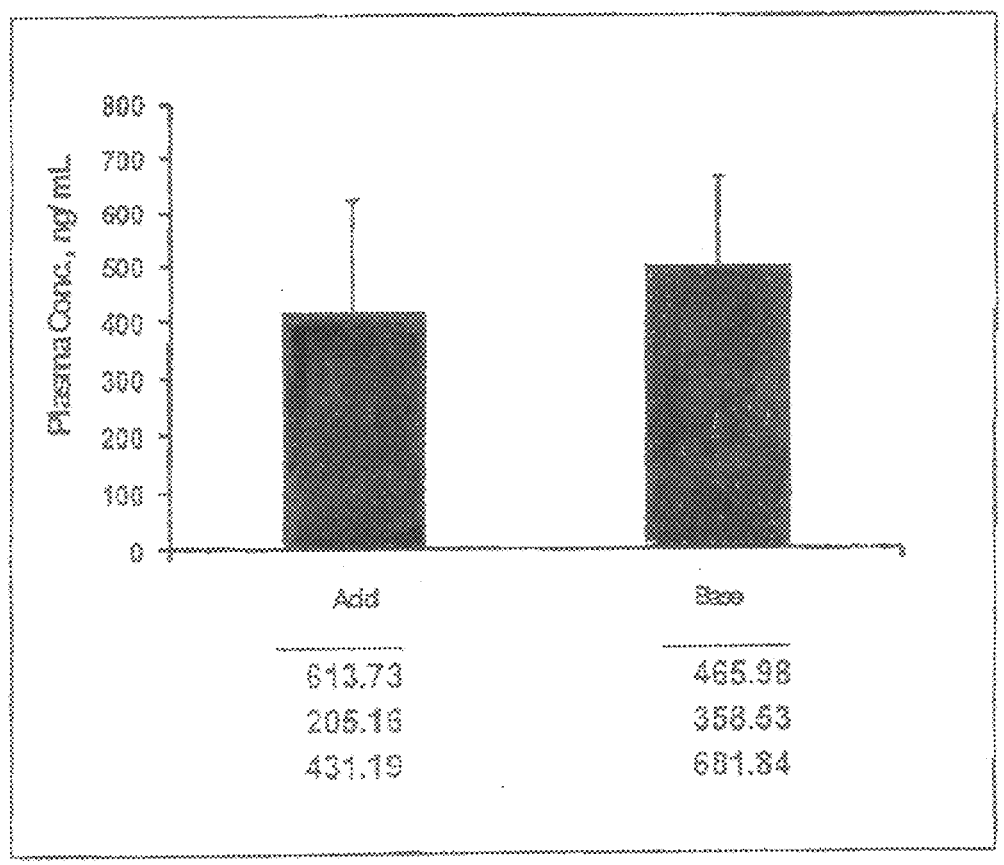
FIG. 1: Plasma concentration in young rats after administration of capsules (approximately 150mg/mL).

| | CBT1 | | | CBT1-2HCl | | |
|---|---|---|---|---|---|---|
| | Animal # | Plasma Conc. (ng/mL) | Dose normalized (ng/mL/mg/kg) | Animal # | Plasma Conc. (ng/mL) | Dose normalized (ng/mL/mg/kg) |
| Suspension 200 mg/kg | 76 | 735.40 | 3.68 | Liquid 200 mg/kg | 79 | 252.20 | 1.26 |
| | 77 | 360.10 | 1.80 | | 80 | 712.90 | 3.56 |
| | 78 | 668.40 | 3.34 | | | | |
| Capsules ~230 mg/kg | 64 | 141.90 | 0.72 | Capsules ~230 mg/kg | 67 | 645.40 | 3.23 |
| | 65 | 51.00 | 0.26 | | 68 | 575.00 | 3.47 |
| | 66 | 307.50 | 1.53 | | 69 | 299.90 | 1.23 |

Note: All doses are reported as the base equivalent.

FIG. 2: Rat plasma concentrations and dose normalized plasma concentrations at two hours after oral gavage with higher dose of d-tetrandrine and d-tetrandrine-2HCl.

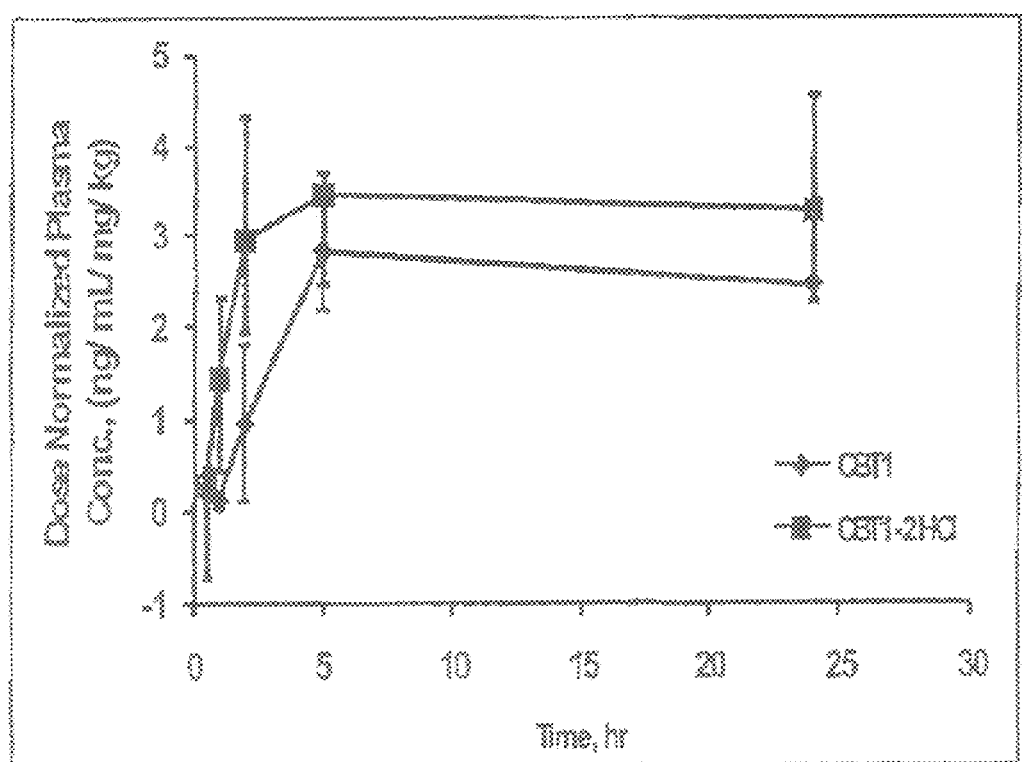
FIG. 3: Dose normalized plasma d-tetrandrine concentrations in rats over 24 hours. Animals were administered approximately 230mg/kg in capsules via oral gavage.

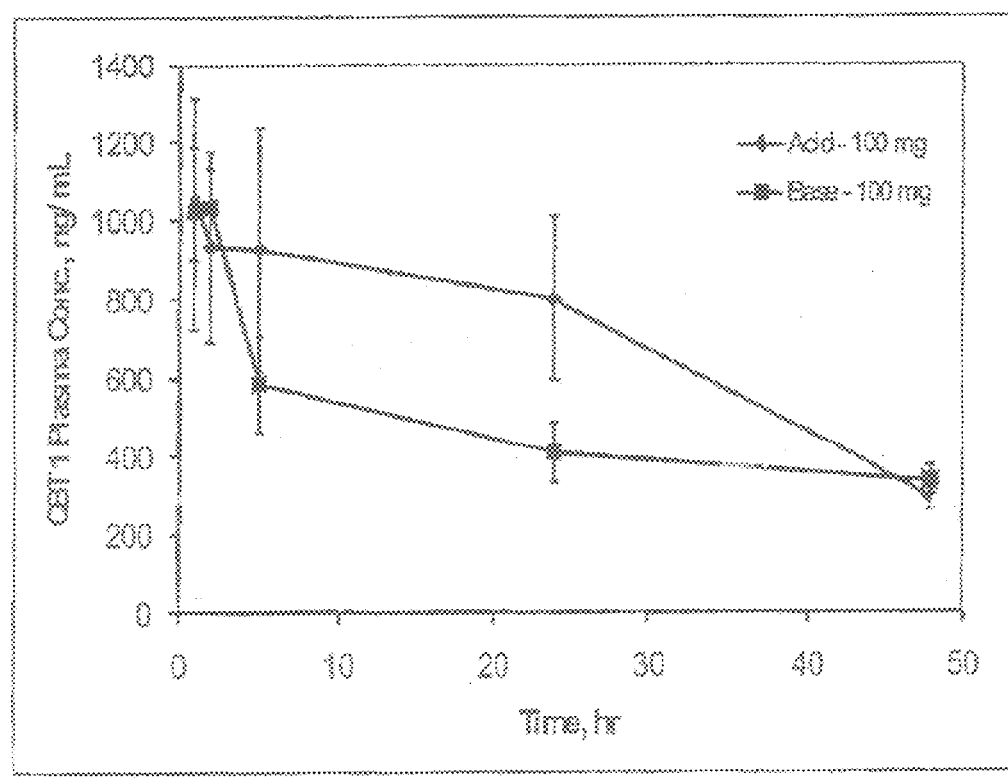
FIG. 4: D-tetrandrine plasma concentrations in rats following 100mg/kg dose of d-tetrandrine or d-tetrandrine-2HCl.

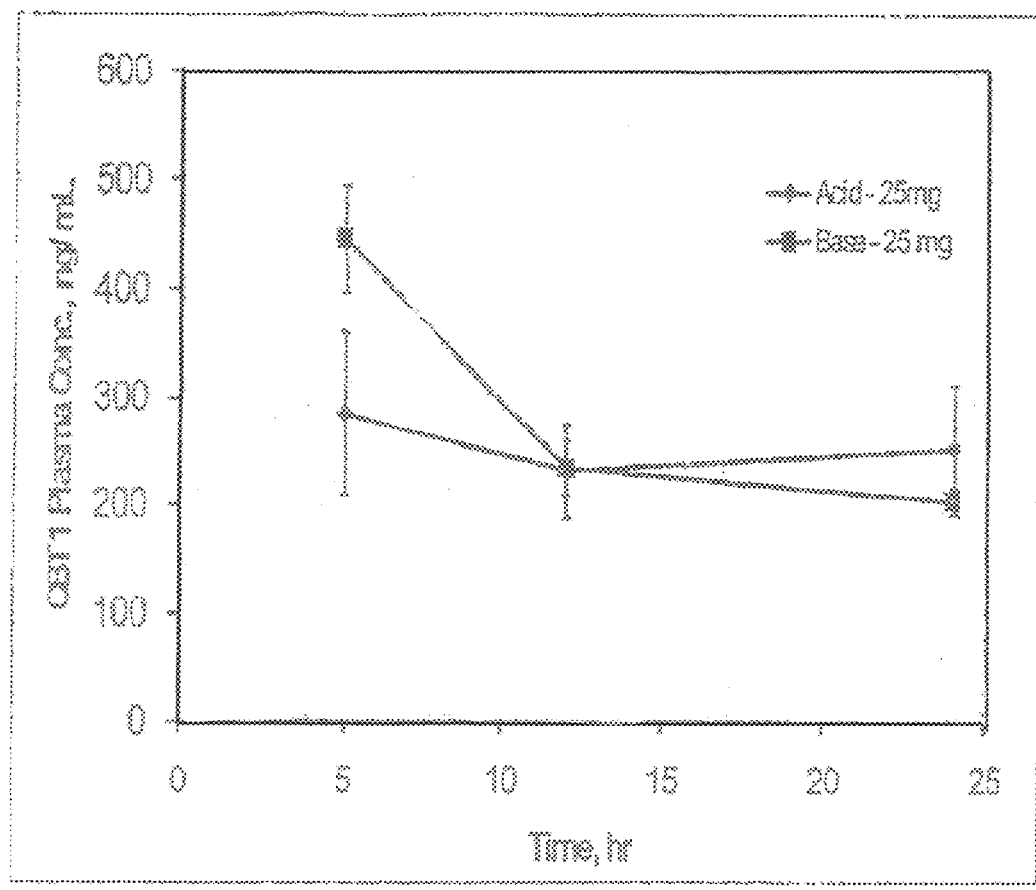
FIG. 5: D-tetrandrine plasma concentrations in rats following 25mg/kg dose of d-tetrandrine or d-tetrandrine-2HCl.

| Treatment | Formulation | AUC$_{0-24}$ (ng·hr/ml) | 95% Confidence Interval | | z-score | Two tailed p-value acid vs. base |
|---|---|---|---|---|---|---|
| | | | Lower | Upper | | |
| 100mg/kg | Acid | 33460 | 22299 | 44620 | 1.9 | 0.06 |
| | Base | 21890 | 17523 | 26256 | | |
| 25mg/kg | Acid | 4723 | 3509 | 5937 | 0.48 | 0.69 |
| | Base | 5026 | 4417 | 5635 | | |

FIG. 6: Estimate of the areas under the time concentration curve using the Bailer method indicate that the formulations are not different at a statistically significant level (p>0.05).

TETRANDRINE PHARMACEUTICAL FORMULATIONS

CROSS REFERENCE TO RELATED APPLICATIONS

The present application claims the benefit of U.S. Provisional Patent Application No. 61/700,701, entitled TETRANDRINE PHARMACEUTICAL FORMULATIONS AND METHOD, filed on Sep. 13, 2012, the entire contents of which are incorporated by reference.

FIELD AND BACKGROUND OF THE INVENTION

The present invention relates to pharmaceutical formulations of a family of bishenzylisoquinoline alkaloids. The specific family is referred to herein as the "tetrandrine family."

The tetrandrine family bisbenzylisoquinolines have two nitrogen locations and hence can exist in the free base form or as a mono or di-acid salt. Because of the enhanced solubility of the salt form of pharmaceutical ingredients, the salt forms are used in formulating pharmaceutical compositions. The active ingredient thus solubilizes more quickly and enters the bloodstream faster.

SUMMARY OF THE INVENTION

In the present invention, it has been surprisingly found that the free base formulations of tetrandrine family members, especially d-tetrandrine, are absorbed into the bloodstream substantially as rapidly as formulations of the di-acid salt members of the family. Thus, the present invention comprises pharmaceutical formulations and methods of formulating and using same in the treatment of cancer and other diseases, comprising:

a free base member of the tetrandrine family having the following structural formula:

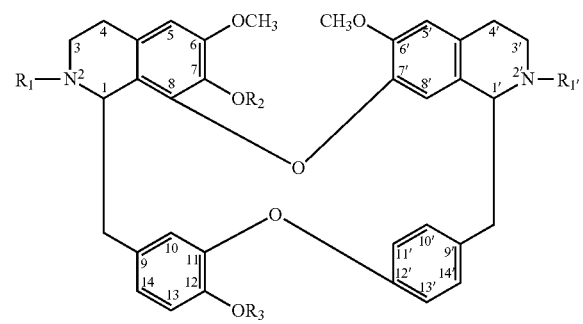

where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen, and a pharmaceutical carrier. Preferably, the family is the d-tetrandrine family, in which said chemical structure has the "S" isomeric configuration at the C-1' carbon location, and most preferably comprises d-tetrandrine.

BRIEF DESCRIPTION OF THE DRAWINGS

FIG. 1 shows the plasma concentration of d-tetrandrine in young rats, for the acid salt and the free base, using capsules of approximately 150 mg/mL.

FIG. 2 shows the rat plasma concentrations and dose normalized plasma concentrations at two hours after oral gavage with higher dose of d-tetrandrine and d-tetrandrine-2HCl.

FIG. 3 shows the dose normalized plasma d-tetrandrine concentrations in rats over 24 hours, and animals were administered approximately 230 mg/kg in capsules via oral gavage;

FIG. 4 shows the d-tetrandrine plasma concentrations in rats following 100 mg/kg dose of d-tetrandrine or d-tetrandrine-2HCl;

FIG. 5 shows d-tetrandrine plasma concentrations in rats following 25 mg/kg dose of d-tetrandrine or d-tetrandrine-2HCl; and FIG. 6 shows an estimate of the area under the time concentration carve using the Bailer method indicating that the formulations are not different at a statistically significant level ($p > 0.05$).

DESCRIPTION OF THE PREFERRED EMBODIMENT

The tetrandrine family members have been found effective in treating multi-drug resistance in a variety of diseases and conditions, including cancer and malaria. See U.S. Pat. Nos. 5,025,020; 5,332,747; 6,528,519; 6,911,454; 6,124,315 and 6,962,927. The formulation of these active ingredients into suitable pharmaceutical delivery systems is thus very important.

The tetrandrine family members have the following structural formula:

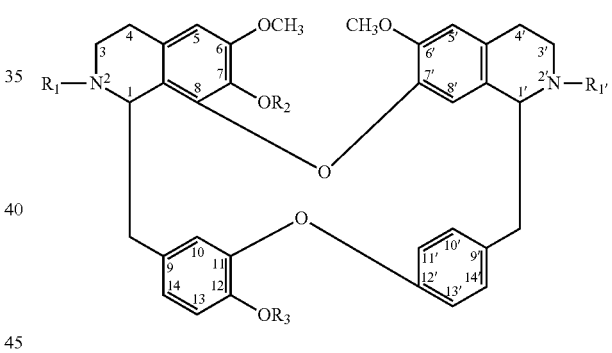

where $R_1$ and $R_1'$ are the same or different shortchained carbon based ligand including without limitation, $CH_3$, $CO_2CH_3$ or H; and $R_2$ is $CH_3$ or $C_2H_5$; and $R_3$ is $CH_3$ or hydrogen; and where the chemical structure preferably has the "S" isomeric configuration at the C-1' chiral carbon location.

The preferred members of the tetrandrine family include the following representative examples, which are not intended to be exhaustive: d-tetrandrine, isotetrandrine, hernandenzine, berbamine, pycnamine, phaeanthine, obamegine, ethyl fangchinolinc and fangchinoline. In all of these examples, $R_1$ and $R_1'$ constitute the methyl group. Variation within the group occurs in that $R_2$ and $R_3$ may constitute either a methyl group or hydrogen, and the isometric configuration of the compounds at the C-1 and C-1' chiral carbon positions is either R (rectus) or S (sinister). The rules for R and S configuration can be found in Morrison and Boyd, "Organic Chemistry," 4th Edition, copyright 1983 by Allyn and Bacon, at pp. 138-141. In addition, hernandezine includes a methoxy group at the C-5 position.

The most preferred member of the claimed tetrandrine family is d-tetrandrine. Methods for extracting and/or purifying, d-tetrandrine are disclosed in U.S. Pat. No. 6,218,541 and in Published Patent Application No. 2011/0105755.

A bioequivalence study in rats was conducted to compare the rate and extent to which the active drug ingredient (d-tetrandrine) is absorbed from a free base versus a hydrochloride salt. The drug ingredients were formulated in capsules by the University of Kentucky Center for Pharmaceutical Sciences and Technology (CPST) to administer equivalent amounts of d-tetrandrine to rats via oral gavage. Dosing syringes, capsule filling apparatus and mini capsules (size 9) appropriate for dosing rats were obtained from Torpac (Fairfield, N.J.).

A single rat per time point (destructive sampling) was used to obtain as much blood volume as possible for the HPLC analysis. This was necessary to accommodate analysis with the current UV based HPLC assay that had extensively been used at CBA Pharma. The JPLC analyses were performed at the CBA Pharma facilities, by a scientist with extensive experience in plasma based assay. Results were provided to a second scientist for evaluation and modeling.

Given the limited information on rat d-tetrandrine pharmacokinetics (PK), the studies were conducted in stages. A preliminary study (pilot) to identify the dose required for adequate assay sensitivity was first conducted using approximately 25 mg/kg and approximately 120 mg/kg doses administered in capsules. Four animals per dose level per formulation (acid or base) were administered drug. Sprague-Dawley rats were used for these studies and were obtained from Harlan Laboratories at least one weak prior to the experiments to allow animals to recover from shipping stress and to acclimate. Animals weighed 200-250 g at the time of the experiments. Animals were euthanized one hour after drug administration and blood was collected in EDTA containing tubes via cardiac puncture and rapidly centrifuged to separate the plasma. Typically, enough plasma was obtained to afford duplicate sample analysis. The plasma was stored at −80° C. until it was transported to CBA Pharma facilities in Styrofoam containers containing dry ice. The results of these experiments indicated that a larger dosage per unit of body mass would be required.

However, multiple capsules required for dosing higher doses were contributing to the pharmacokinetic variability observed in initial pilot studies. Thus in subsequent studies, younger and smaller animals were administered doses of approximately 150 mg/kg, and blood samples were obtained two hours after drug administration. These smaller animals were more difficult to dose because the size of the tablet. Three animals from the "acid" group and two animals from the "base" group were excluded based on the technician's judgment that some tissue damage had been done to the animals during the gavage dosing. These younger animals (50-60 grams each) yielded smaller blood volumes, but adequate plasma volume was obtained for HPLC analysis after plasmas were pooled from two animals per sample. As seen in FIG. 1, the concentrations were comparable between the two formulations. The values below each bar show the actual data obtained from the pooled samples. For this analysis, the quality control samples were within an acceptable nominal value range. The variability observed is believed due to the fact that the drug would be cleared/distributed after absorption to lower levels than those observed at two hours.

This second pilot study indicated that a higher dose would be required in order to measure samples for 24 hours. Thus three animals were administered 200 mg/kg of each the acid and base formulations in liquid or suspension, respectively, to determine if the dosing and/or variability would improve. The base did not dissolve in water and therefore was used in suspension. The solution, and suspension were prepared in water with 0.25% carboxymethylcellulose to facilitate fluidity during dosing. Samples were collected at 30 minutes, 1, 2, 5 and 24 hours after administration of capsules.

FIG. 2 lists the data obtained from the animals receiving the capsules, and the liquid/suspension formulations. No statistical difference was observed among the dose preparations (Student 1-test, two-tailed, p>0.05). Likewise, no statistical difference was observed among the d-tetrandrine and d-tetrandrine-2HCl formulations Student 1-test, two-tailed, p>0.05. The pharmacokinetic profile using the dose normalized concentrations is also presented in FIG. 3.

In some cases the plasma concentrations could not be determined due to extremely high interfering peaks. Thus following the results of these studies, one final study was performed using the liquid/suspension formulation and a dose of 100 mg/kg which would translate to approximately 150 mg/m$^2$. Based on average human body surface area of 1.7 m$^2$, these doses would translate to approximately 350 mg and approximately 90 mg flat doses in humans.

Three spiked samples were also included in the last batch of samples. These "quality control" sample concentrations were only known to the technician who was given a range from which to choose concentrations. These samples were not identified as "quality control" samples until after the HPLC analysis was complete and the results were sent to the University of Kentucky.

Six animals per time point were used in the last experiment. The sampling times were 1, 2, 5, 24 and 48 hours for the 100 mg/kg dose and 5, 2 and 24 hours for the 25 mg/kg group. All animals and procedures were as described above. The liquid and suspension formulations were prepared under sterile conditions at the CPST and were administered by oral gave. No complications were observed with any of the animals daring the closing. Animals received dose volumes of 1 ml/200 g. The spiked quality control samples were within acceptable limits of the expected values (115 vs 150 ng/mL (103.4%); 176.6 vs 200 ng/mL (88.3%) and 299.4 vs 300 (99.8%). As depicted in FIG. 4, d-tetrandrine plasma concentrations were well above the qualification limit of the HPLC assay for 48 hours. However, the results were highly variable within each formulation at each time point.

Similarly, the plasma concentrations were above quantitation limits in rats receiving 25 mg/kg doses even at 24 hours. Here again, the data were variable within each formulation. The plasma concentrations measured at 5, 12 and 24 hours are presented in FIG. 5.

The bioequivalence of the two formulations was assessed at the 100 mg/kg dose level, using estimates of the area under the time concentration curve. The method of Bailer[1] was used to estimate the AUC for each formulation and to obtain error size for statistical comparisons. The relative increase of the AUC from the 25 mg/kg to the 100 mg/kg dose within a formulation was compared using AUC estimates obtained with the simple linear trapezoid method.

[1] Bailer, A. J., *Testing for the equality of area under the curves when using destructive measurement techniques.* Pharmacokinet Biopharm, 1988. 16(3): p. 303-9.

Based on the AUC estimates obtained using the Bailer method (FIG. 6), no statistical or otherwise significant difference was found among the acid and base formulations.

The dosage level in humans will vary from case to case. However, it is anticipated that one would typically administer the tetrandrine family member drug at from about 50 to about 1000 mg per square meter per day, more preferably 250-700, and most preferably about 500, for from about 4 to about 14 days, during the course of treatment with a principle drug for treating the disease being treated. The ratio of the tetrandrine family member to a principle drug will also vary from patient to patient, within a range of from about 0.04 to about 170, more typically from about 1 to 100.

The preferred formulations comprise a free base member of the d-tetrandrine family combined with a suitable pharmaceutical carrier. The pharmaceutical carrier can be a liquid or a solid composition. A liquid carrier will preferably comprise water, possibly with additional ingredients such as 0.20-0.30%, preferably 0.25%, carboxymethylcellulose. The solid carrier or diluent used is preferably pregelatinized starch. It may also be formulated with other ingredients, such as colloidal silicone dioxide, sodium lauryl sulfate and magnesium stearate.

Exemplary capsule formulations include the following:
30 mg Tetrandrine
384 mg Pregelatinized Starch NF (Starch 1500)
4.4 mg Colloidal Silicon Dioxide (Cab-O-Sil M5)
0.4 mg Sodium Lauryl Sulfate NF
1 mg Magnesium Stearate NF
200 mg Tetrandrine
25.7 mg Pregelatinized Starch 1500 NF
1.5 mg Silicon Dioxide USP
0.25 mg Sodium Lauryl Sulfate NF
1.25 mg Magnesium Stearate USP The 200 mg capsule formulation is most preferred. The most preferred dose of about 500 mg/square meter/day is roughly 1000 mg per day for a 190 pound patient six feet tall. Such a patient can fulfill the dosage requirements by taking five capsules during the course of the day, for example three in the morning and two in the evening, or one at a time spaced out over the day. A woman weighing 125 pounds at a height of five feet six inches would require four 200 mg capsules during the course of the day.

The various diseases which have been treated using tetrandrine family members in conjunction with principle drugs for treating the diseases, and the principle drugs used, are disclosed in U.S. Pat. Nos. 5,025,020; 5,332,747; 6,528,519; 6,911,454; 6,124,315 and 6,962,927.

Of course, it is understood that the above disclose some embodiments of the invention, and that various changes and alterations can be made without departing from the scope of the invention as set forth in the attached claims and equivalents thereof.

The invention claimed is:

1. A pharmaceutical formulation comprising: free base d-tetrandrine in a pharmaceutical carrier solution containing 0.20-0.30% carboxymethylcellulose.

2. A pharmaceutical formulation comprising: free base d-tetrandrine in a pregelatinized starch pharmaceutical carrier.

3. The pharmaceutical formulation of claim 2 also comprising: colloidal silicon dioxide, sodium lauryl sulfate and magnesium stearate.

4. The pharmaceutical formulation of claim 2 comprising:
50 mg Tetrandrine
384 mg Pregelatinized Starch NF (Starch 1500)
4.4 mg Colloidal Silicon Dioxide (Cab-O-Sil M5)
0.4 mg Sodium Lauryl Sulfate NF
1 mg Magnesium Stearate NF.

5. The pharmaceutical formulation of claim 2 comprising:
200 mg Tetrandrine
25.2 mg Pregelatinized Starch 1500 NF
1.5 mg Silicon Dioxide USP
0.25 mg Sodium Lauryl Sulfate NF
1.25 mg Magnesium Stearate USP.

* * * * *